United States Patent [19]

Hale

[11] Patent Number: 4,563,249
[45] Date of Patent: Jan. 7, 1986

[54] ELECTROANALYTICAL METHOD AND SENSOR FOR HYDROGEN DETERMINATION

[75] Inventor: John M. Hale, Meinier, Switzerland

[73] Assignee: Orbisphere Corporation Wilmington, Succursale de Collonge-Bellerive, Collonge-Bellerive, Switzerland

[21] Appl. No.: 493,316

[22] Filed: May 10, 1983

[51] Int. Cl.$^4$ ............................................. G01N 27/46
[52] U.S. Cl. ..................................... 204/1 T; 204/415
[58] Field of Search ...................... 204/1 P, 1 T, 415

[56] References Cited

U.S. PATENT DOCUMENTS

| | | | |
|---|---|---|---|
| 3,001,918 | 9/1961 | Czuha | 204/430 |
| 3,098,813 | 7/1963 | Beebe et al. | 204/415 |
| 3,149,921 | 9/1964 | Warner | 204/1 T |
| 3,260,656 | 7/1966 | Ross | 204/415 |
| 3,325,378 | 6/1967 | Greene et al. | 204/415 |
| 3,468,781 | 9/1969 | Lucero | 204/415 |
| 3,509,034 | 4/1970 | Paine | 204/415 |
| 3,787,308 | 1/1974 | Malaspina et al. | 204/415 |
| 3,948,746 | 4/1976 | Poole | 204/415 |
| 4,132,616 | 1/1979 | Tantram et al. | 204/415 |
| 4,293,399 | 10/1981 | Belanger et al. | 204/415 |

OTHER PUBLICATIONS

Niedrach et al., Anal. Chem. 1982, vol. 54, pp. 1651–1654.
Gruniger et al., Helvetica Chemica Acta, vol. 61, Fasc 7, (1978), Nn 226, p. 2375.

Primary Examiner—T. Tung
Attorney, Agent, or Firm—Oblon, Fisher, Spivak, McClelland & Maier

[57] ABSTRACT

A method of and a sensor for quantitative electroanalytical determination of elemental hydrogen in a fluid medium are disclosed. A membrane enclosed amperometric cell is used that has at least two electrodes in contact with an aqueous electrolyte to provide a reaction impedance of the cell; the electrolyte is separated from the fluid medium by a membrane that is permeable to elemental hydrogen but substantially impermeable to the electrolyte and provides a membrane impedance of the cell; the electrodes include an anodic hydrogen sensing electrode and a cathodic counter electrode; the sensing electrode has a polished surface consisting of a platinum metal; further, the membrane is selected such that the membrane impedance exceeds the reaction impedance sufficiently to provide for membrane-controlled operation of the cell.

13 Claims, 2 Drawing Figures

ELECTROANALYTICAL METHOD AND SENSOR FOR HYDROGEN DETERMINATION

CROSS-REFERENCE TO RELATED CASES

This application generally relates to subject matter disclosed in the following U.S. applications: U.S. application Ser. No. 773,163, filed Mar. 1, 1977, issued as U.S. Pat. No. 4,096,047; U.S. application Ser. No. 164,291, filed June 30, 1980, issued as U.S. Pat. No. 4,325,797; U.S. application Ser. No. 319,708, filed Nov. 9, 1981, issued as U.S. Pat. No. 4,372,021; and U.S. application Ser. No. 345,536, fild Feb. 3, 1982.

BACKGROUND OF THE INVENTION (a) Field of the Invention

This invention relates generally to the art of amperometric measurement and to devices of the type used for quantitative electrochemical analysis methods where the concentration of an electroactive species in a fluid medium is to be measured or monitored; more particularly, this invention relates to an improved method of quantitative electroanalytical determination of elemental hydrogen.

The invention further relates to an amperometric hydrogen sensor.

(b) Description of the Prior Art Electrochemical cells of the type used for quantitative electrochemical analysis are well known in the art and generally include a working or sensing electrode having a defined or electroanalytically effective surface, a counter electrode, an optional guard electrode, an electrolyte in contact with the electrodes and a membrane that is substantially impermeable to the electrolyte but is permeable to the electroactive species of interest and defines the sensor face in terms of a barrier between the electrolyte space, notably the electrolyte film on top of the sensing electrode, and the ambient medium that contains the electroactive species of interest.

For amperometric analytical operation, the working electrode of such a cell arrangement is polarized by a constant DC voltage to furnish a current whose steady state magnitude is proportional to the activity of the electroactive species of interest. Cells of this type and their operation and use for determination purposes are discussed in the following illustrative U.S. Pat. Nos. 2,913,386, 3,071,530, 3,223,608, 3,227,643, 3,325,378, 3,372,103, 3,406,109, 3,429,796, 3,515,658, 3,622,488 and 4,096,047 as well as in British Published Application No. 1,013,895.

The above mentioned U.S. Pat. No. 2,913,386 to Leland E. Clarke considered as the pioneering patent already teaches that methods of this type are suitable for use in determining either electro-reducible or electro-oxidizable gases using electroanalytical devices also called "membrane-covered polarographic detectors". As the term "polarographic" has also been used for techniques based on the dropping mercury electrode and operating either in a voltametric or galvanic mode, the term "membrane-enclosed amperometric cell" or MEAC is used herein to refer to electroanalytical probes such as the "Clark Cell" and modifications thereof including those that use guard electrodes and various devices to improve operation, reliability, sensitivity and maintenance.

However, while the determination of electro-reducible gases, notably of oxygen, by means of MEAC sensors is widely accepted (cf. for example Hitchman, M. L., Measurement of Dissolved Oxygen, ISBN 0-471-03885-7), previous attempts to use this technique for determination of electro-oxidizable gases, notably hydrogen, have not met with comparable success.

To the best of applicant's knowledge, measurement of hydrogen with a MEAC type sensor was first mentioned by Sawyer et al, Anal. Chem. 31, 2 (1959) who reported that their attempt to detect hydrogen by this principle was totally unsuccessful. Then, Greene, M. W. et al, have disclosed a hydrogen sensing method by means of a modified MEAC in the above mentioned U.S. Pat. No. 3,325,378, and that patent cites various fields of technology where hydrogen sensing is important, e.g. detection of hydrogen leakage whenever hydrogen is used as a reactant, coolant or fuel, notably for prevention of forming explosive mixtures of hydrogen and air.

While the need for sensing and quantitative determination of hydrogen has by no means diminished, the electroanalytical method using MEAC type sensors has not been found to be generally suitable and hydrogen sensors have not been made available commercially so far.

The feature common to prior art hydrogen sensing with a MEAC according to the Greene et al patent and according to various other reports (von Gruniger et al, Helv. Chim. Acta 61 (1978) 2375; Srinivasan et al, Anal. Chem. 53 (1981) 928; Mills et al, Anal. Chem. 53 (1981) 1254; Niedrach et al, Anal. Chem. 54 (1982) 1651) is that stability of measurements and notably the absence of detrimental drift generally required some sort of surface enlargement at the anodic sensing surface made of a platinum metal, e.g. by using etching techniques or by using micro-crystalline layers of the type obtained by electrolytic platinization or deposition techniques including layers of platinum-black.

As disclosed in the Greene et al Patent, platinum-black is preferred over an etched platinum surface as the anodic sensing surface because it produces a more stable output, and it is the consistent teaching of the art that surface increase or "roughening" leading to enhancement and activation of the platinum sensing area is required at the anodic electrode of MEAC type hydrogen sensors thus precluding the use of conventionally polished, i.e. substantially smooth platinum metal anodes for that purpose.

The use of polished smooth electrode surfaces of noble metals including platinum is quite conventional in MEAC type sensors for oxygen measurement and the advantages of using a smoothly polished platinum surface over platinum-black or other area-enhanced platinum surfaces at the sensing electrode is apparent to everybody familiar with the electroanalytical art: reproducibility and definition of the sensing area as well as ease of manufacture, maintenance, and maintenance control are, of course, far better when using smoothly polished platinum surfaces and nobody in the electroanalytical art would willingly give up these advantages unless this was believed to be absolutely unavoidable.

From this it will be apparent that prior art hydrogen sensing methods with MEAC sensors were assumed to be inoperative with smooth anodic sensing surfaces of platinum metal if an output of acceptable stability was to be obtained.

OBJECTS AND SUMMARY OF THE INVENTION

Accordingly, it is a main object of the invention to provide for an improved method of quantitative electroanalytical determination of elemental hydrogen with a MEAC wherein the anodic hydrogen sensing electrode has a substantially smooth sensing surface and yet produces an output of acceptable stability.

Another object is an improved method providing for simplicity, precision, stability, ruggedness and convenience in the operation of a MEAC type sensor for quantitative hydrogen determination.

Another object is a MEAC type hydrogen sensor having a smoothly polished anodic sensing surface made of platinum metal yet producing an output of acceptable stability.

Further objects will become apparent as the specification proceeds.

It has been found according to the invention that the above objects and further advantages will be achieved if (a) the anodic hydrogen sensing electrode has a substantially smooth sensing surface consisting essentially of a platinum metal and (b) if—as a corollary—the membrane impedance of the MEAC is maintained to exceed the reaction impedance sufficiently for providing a membrane-controlled, i.e. diffusion-controlled, operation of the MEAC.

While this teaching is abstract and backed-up by a relatively complex mathematical treatment as explained further below, its practical implication is extremely simple and effective. In fact, the novel hydrogen sensing method can be practiced, in essence, with conventional sensors simply by selecting the membrane for reduced hydrogen diffusion according to criteria that can be determined easily as explained below.

It is of notable interest that the prior art of MEAC hydrogen sensing has concentrated in essence on anode surface modifications assuming that the seemingly inherent unsuitability of polished platinum surfaces for stable hydrogen sensing was the problem to be solved and this may be the main reason why no MEAC hydrogen sensor is available commercially nor used for routine processing or manufacturing operation.

With the assumption of prior art that the activity or reactivity of the sensing anode should be increased, there was no apparent reason to more closely review the role of the membrane as, e.g. according to the above mentioned U.S. Pat. No. 3,325,378 to Greene et al, membrane materials and membrane thicknesses of the type conventionally used for oxygen sensing, e.g. 1 mil Teflon (type PTFE=polytetrafluoro ethylene), polyethylene and polypropylene, were believed to be suitable for hydrogen sensing as well.

The present invention is based upon the insight that instead of taking an arbitrary membrane and attempting to optimize the activity or role of the anode, one might start from an optimum, i.e. polished platinum, anode surface and try to optimize the role of the membrane. The roles of anode and membrane in a MEAC can be quantified by assuming that the magnitude of the electric current must be equivalent (in steady state and written in appropriate units) to the net entry of hydrogen into the sensor through the membrane, on the one hand, and to the rate of disappearance of hydrogen due to its reaction (oxidation) at the anode, on the other hand.

Accordingly, the experience of prior art to the effect that an increased anode activity was required for stable results could be re-interpreted in the sense that instead of increasing the anode reactivity (i.e. hydrogen reaction rate at the anode), one could decrease diffusion of hydrogen through the membrane.

As will be shown below, the soundness of this inversion can be verified both empirically and mathematically and the result of the inversion is that hydrogen determination with good response and stability will be achieved—in contrast to the teachings of prior art—when using a polished platinum anode if the operation of the MEAC is "membrane-controlled" (hydrogen diffusion or permeation through the membrane is a limiting factor) and not "reaction-controlled" (rate of hydrogen reaction at the anode is a limiting factor).

DEFINITION OF TERMS AND DISCUSSION OF PREFERRED EMBODIMENTS

The term "determination of elemental hydrogen in a fluid medium" is intended to encompass diverse types of measuring the hydrogen content of or concentration in a fluid medium ranging from sensing small or even minute amounts, e.g. in the ppb, ppm or percent range, of gaseous hydrogen dissolved in liquid fluids, (including water and aqueous media or non-aqueous media) or admixed with other gaseous fluids (e.g. nitrogen, oxygen, carbon dioxide, hydrogen halides, ammonia, water vapor and mixtures including air) to the determination of the purity of gaseous hydrogen, e.g. in the 50 to 100% range.

The term "amperometric cell" refers to MEAC or Clarke type cells as explained above with reference to a number of patents.

The term "comprising at least two electrodes" indicates that the cell has at least one first or sensing electrode which, in hydrogen sensing, is the anode and at least one second or counter electrode which, in hydrogen sensing, is the cathode; the cell may have a third or guard electrode of the type disclosed in German Pat. No. 2 851 447 used in the present invention at substantially the same potential as the sensing anode to guard the latter. While each electrode might consist of two or more segments, this is not generally preferred for the anode or the guard electrode.

The counter electrode is the point of reference with respect to which the potential of the hydrogen sensing anode is determined; preferably, the cathode surface area is larger than the anode surface area, typically by a factor in the range of from 2-10.

The term "electrodes in contact with an aqueous electrolyte" generally implies that a surface area of each electrode is exposed to the electrolyte; the electrolyte exposed surface area or sensing surface of the anode consists of a platinum metal as explained below and should remain unchanged; the electrolyte exposed surface of the cathodic counter electrode need not be well defined but is preferably substantially greater than the sensing surface of the anode, e.g. by a factor of at least 3 and preferably at least 5; conventional cathode materials including silver/silver chloride, silver/argentous ion as well as various redox systems such as iodine/iodide or ferrous/ferric exchanging on a noble metal cathode, such as gold or platinum, are suitable in general. Generally, the cathode should satisfy the criterion that its products be un-oxidizable at the anode and do not interfere with operation of the cell.

Suitable aqueous electrolytes include those disclosed in the above mentioned patents and publications insofar as related to hydrogen sensing; for example, chloridic electrolyte compositions disclosed in the Greene et al patent are suitable but need not be buffered for neutrality; in fact, acidic electrolytes including or consisting essentially of normal (N) aqueous mineral acids, such as hydrochloric acid, sulfuric acid, are suitable and may be preferred.

"Reaction impedance" is intended to refer to the electrode or anode reaction impedance and can be quantified as the reciprocal value of the rate of the hydrogen (oxidation) reaction at the anode ($H_2 \rightarrow 2H^+ + 2e$), wherein e represents an electron in the anode); for practical application of the invention, such quantification is not required, however. A high value of the reaction impedance corresponds, of course, with a low rate of hydrogen oxidation at the anode.

"Membrane impedance" is intended to refer to the hydrogen diffusion impedance caused by the membrane and can be quantified as the reciprocal value of the rate of hydrogen diffusion (permeation) through the membrane; again, such quantification is not required for practical use of the invention but specific data for hydrogen permeability of many commercially available polymer films are obtainable or can be measured easily.

For practicing the inventive method it is important that the membrane impedance exceeds the reaction impedance sufficiently to provide for membrane-controlled cell operation ("M/C-operation" hereinbelow), i.e. prevent reaction-controlled cell operation ("R/C-operation" hereinbelow) and maintaining this requirement is essential to the invention as a corollary to using an anode having a smooth sensing surface of a platinum metal.

In view of this connexion it is sufficient for many purposes of the invention to check for the result, i.e. maintenance of M/C-operation or avoidance of R/C-operation, with a given MEAC including a given polished platinum anode and a given electrolyte. A first convenient method is to measure and record the dependence of the current of a given sensor upon the partial pressure of hydrogen in an ambient or test gas (termed "current/pressure dependence" hereinbelow) for membranes made of different materials and/or different thicknesses.

For reasons that are apparent from the mathematical model explained in the examples, the current/pressure dependence will be linear only in M/C-operation according to the invention. Also, a test based upon diffusion theory (cf. Hale, J. M., et al, J. Electroanal. Chem., 107 [1980] 281-294) and measurements of the time of response of a MEAC to a step change of hydrogen explained in more detail below will show a linear dependence of the reduced time parameter upon time only when a MEAC operates in M/C-mode while the same dependence will be clearly non-linear upon R/C-operation. Alternatively or complementarily, the time dependence or drift (i.e. negative stability) of otherwise identically obtained hydrogen determinations can be used to verify M/C-operation according to the invention; for example, such drift towards lower values upon repetition will generally be less than 1% per day in M/C-operation or more than 10% per day in R/C-operation.

Such ease of indirect control of M/C- versus R/C-operation is advantageous because actual hydrogen permeation will not only be dependent upon a membrane material with a specific nominal hydrogen permeability (frequently expressed in molar units such as micromoles ($\mu$mol) or nanomles (nmol) of hydrogen per membrane surface, pressure differential and time, e.g. $\mu mol \cdot m^{-2} \cdot bar^{-1} \cdot sec^{-1}$) of a given organic polymer film and a specific nominal thickness, e.g. in micrometers ($\mu$m) or mils (0.001 inch) but also from such incidental factors as intended or accidental stretching of the membrane.

A number of non-limiting examples of organic polymers available commercially in the form of films in various gauges and suitable for the invention are given in the Table I below, it being understood that, in essence, any given organic polymer film may be suitable at a particular thickness. Thus, it is the actual "permeation value" of a membrane that essentially determines the rate of hydrogen diffusion; "permeability" is a unit that is frequently given without exact reference to actual membrane thickness while the "permeation factor" cited below relates to a gauge or thickness unit (micrometers).

Generally, suitable membranes are those having a hydrogen permeation factor of below 10 and preferably below 1 ($nmol \cdot \mu m \cdot m^{-2} \cdot Pa^{-1} \cdot s^{-1}$); membranes with a permeation factor of below 1 can be used at typical gauges of 1 mil (25.4 $\mu$m) or less, e.g. down to 0.5 mil (ca. 10 $\mu$m). Membranes with permeation factors in the range of from 1 to 10 may be suitable if used in a higher gauge, say 2 or 5 mil (50–130 $\mu$m); it will be appreciated that the membrane thickness or gauge should generally be below 300 $\mu$m, preferably below 100 $\mu$m and most preferably below 50 $\mu$m, for many purposes of the invention where a relatively quick response to a step change of hydrogen partial pressure in the ambient fluid is important. On the other hand, very thick membranes, e.g. of about 1 mm, could be used with membrane materials having high hydrogen permeability, e.g. silicone rubber.

The electrolyte used in the inventive method is aqueous. Unbuffered aqueous solutions of inorganic or organic acids are suitable. Preferably, no buffer salts or metal cations are added in making the electrolyte and concentrations in the normality range are suitable, e.g. 0.5 to 2 normal; typical preferred examples are aqueous solution of acids such as sulfuric acid, perchloric acid and nitric acid. Preferably and as far as possible in view of compatibility, corrosion resistance and the like MEAC parameters, the electrolyte chosen should contain anions of as low a polarizability as possible since such anions tend to be adsorbed less on the anode surface and favor a stable operation; the order of polarizability (higher to lower) can be presented as follows: $I^- > Br^- > Cl^- > SO_4^{--}, ClO_4^-, F^-$.

TABLE I

| Polymer name | Symbol | Commercial source and name | Commercial type defined in* | Hydrogen permeation factor** |
|---|---|---|---|---|
| fluorinated ethylene/propylene | FEP | DU PONT (Teflon) | a-62943 | 4 |
| polyfluoroalkoxy polymer | PFA | DU PONT (Teflon) | e-09687 | 5.6 |
| polyvinylfluoride | PVF | DU PONT (Tedlar) | e-43348 | 0.1 |
| copolymer of ethylene and tetrafluoroethylene | ETFE | DU PONT (Tefzel) | a-84012 | 1.57 |
| copolymer of ethylene and | E-CTFE | ALLIED CHEM. | cp-310-10m65 | 0.144 |

TABLE I-continued

| Polymer name | Symbol | Commercial source and name | Commercial type defined in* | Hydrogen permeation factor** |
|---|---|---|---|---|
| monochlorotrifuoroethylene | | (Halar) | | |

Notes:
*specifics of commercial product given in brochure number as shown; brochures published by supplier except for Halar where brochure is printed by Chemplast Inc., Wayne, N.J.
**unit: nmoles · $\mu$m · m$^{-2}$ · Pa$^{-1}$ · sec$^{-1}$ Thus, while film forming organic polymers are suited in general for the invention, halogen-containing homopolymers or copolymers of polyenes, such as FEP, PFA, PTFE, PVF, ETFE and E-CTFE, are preferred, E-CTFE and PVF being particularly preferred.

The term "platinum metal" or "platinum metals" includes metallic platinum (Pt), metals of the "platinum group" including Pd, Rh, Ir, Ru and Os as well as alloys or mixtures of these metals with each other or with noble metals such as gold. Platinum in a substantially pure form is suitable and preferred for many purposes of the invention.

The term "substantially smooth" as used herein to describe the surface quality of the sensing surface is intended to refer to a "glossy", "bright" or "polished" appearance generally defined by a high reflectance of typically above 50%. As opposed to prior art anodes for hydrogen sensing where the surface was "rough" or "black" and the actual surface area exceeded the apparent surface area by a factor of up to many hundreds, a typical smooth anode surface according to the invention is obtained by polishing the platinum metal surface until a glossy and substantially mirror-type surface appearance is obtained; typically, the actual surface area of a smooth surface is less than three times and typically not more than 1 to 2 times the apparent surface area. Suitable methods to measure this ratio are known per se and include double-layer capacity or charge measurements (c.f. Monography by E. C. Potter, Electrochemistry, London, 1956) by measuring the capacity of the surface to be tested at a voltage where hydrogen is evolved by reduction of hydrogen ions and comparing the value obtained with that of a perfectly smooth mercury electrode.

Other suitable methods include charge measurement or adsorptive methods that indicate actual rather than apparent area.

The term "applied voltage" refers to the difference of potential applied between the sensing anode and the cathodic counter electrode; as the reaction rate can be increased by an increase of the applied voltage thus diminishing the reaction impedance, it would seem that the desired M/C-operation for any given membrane impedance could be easily achieved in this manner; however, the threshold for oxidation of water (which is part of the electrolyte) is reached soon (at 1.23 V) and presents a very narrow limitation for decreasing the reaction impedance.

Typical currents when operating the inventive method may depend upon the nature of the electrolyte; for example, when operating in 1N sulfuric acid (aqueous) currents of up to 3 $\mu$A per mm$^2$ of anode area or more may be observed per each bar of partial hydrogen pressure; with chloridic electrolytes lower current levels have been observed and it may be desirable to increase the membrane impedance to the point where the current per bar of partial pressure ($H_2$) is maintained below 1 $\mu$A per mm$^2$ of anode area.

As mentioned above, an acceptable stability of measurement in hydrogen determination according to the invention implies a drift of less than 1% per day. A further advantage of M/C-operation according to the invention is believed to reside in the fact that flow rates (ambient fluid) well below the values required in prior art hydrogen sensing of typically about 1000 ml/min, e.g. at about 200 to 300 ml/min, can be achieved.

MEAC devices suitable for use in the present invention of various types or commercial provenience can be used. A preferred type is that described in the above mentioned U.S. Pat. No. 4,096,047 (pressure seal) with a central electrode coated with polished platinum and with or without the modifications disclosed in the above mentioned U.S. Pat. No. 4,325,797 (membrane holding device) and the above mentioned German Pat. No. 2 851 447 (guard electrode).

A commercially available MEAC device is that sold by Orbisphere Laboratories, Geneva, Switzerland, under model No. 2115 (Pt) which is essentially the model sold for oxygen sensing except that the central electrode is provided with a 300 $\mu$m platinum layer by rolling of platinum sheet onto the steel base.

Other materials generally required for amperometry including a voltage source, temperature compensating means, amplifiers, recorders, electrolytes etc. are available commercially as well and suitable membranes can be cut from commercially available polymer films of the type indicated above.

BRIEF DESCRIPTION OF THE DRAWINGS

The present invention is illustrated by way of example and not limitation in the Figures of the accompanying drawings in which.

DISCUSSION OF DRAWINGS AND EXAMPLES

Figure 1:
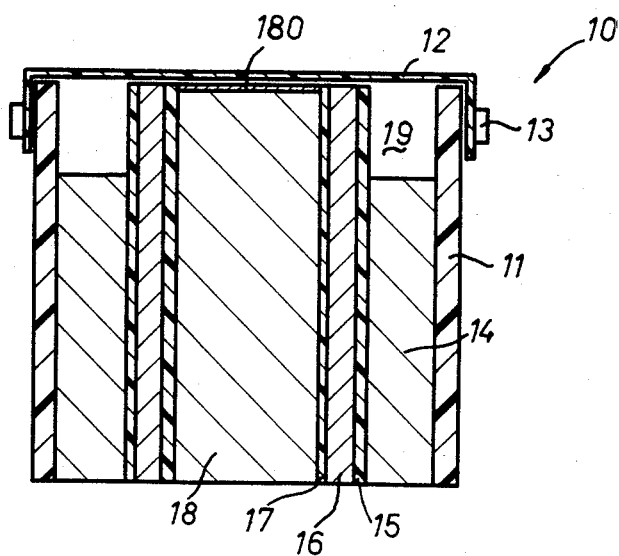
FIG. 1 is a diagrammatic cross-sectional view of a hydrogen sensor embodying the invention.

FIG. 1 shows the diagrammatic cross-section of the structure of a sensor 10 of the type known for oxygen sensing. Sensor 10 has a generally cylindrical shape and includes the following main elements in a substantially coaxial arrangement: outer case 11 supports and holds, at its upper end, a membrane 12 by means of a holding ring 13 and surrounds the counter electrode 14 which in hydrogen sensing—i.e. electrooxidation of elemental hydrogen as explained above—is the cathode. An electrically insulating layer 15 separates the cathodic counter electrode 14 from the adjacent electrode 16 which in this presentation is an optional guard electrode maintained at substantially the same potential as the central or sensing electrode 18 which in hydrogen sensing is the anode. An insulating layer 17 is arranged between the anodic guard electrode 16 and the anodic sensing electrode 18. An electrolyte reservoir 19 is provided to receive and contain an aqueous electrolyte of the type explained above for hydrogen sensing, generally at a pH below 7.

As is known in the art, the electrolyte forms a continuous and preferably very thin layer between membrane 12 and the electrolyte-exposed sensing surface 180 of anode 18.

For the purpose of the invention, surface 180 consists of a platinum metal, e.g. pure platinum, and is substantially smooth, e.g. polished to achieve a reflectance of at least 50% corresponding to a mirror-type surface quality. While the entire anode 18 might be made of a platinum metal, it will be sufficient in general to apply a surface layer layer a thickness of some micrometers, e.g. 5 to 50 μm or millimeter fraction, e.g. 0.1 to 1 mm, onto a substrate, e.g. by rolling or soldering techniques.

In contrast to prior art both in oxygen and in hydrogen sensing, the membrane 12 is not selected for high permeability of the electroactive species of interest but—contrarily—a membrane of limited and preferably low hydrogen permeability is used as explained above to achieve a membrane-controlled (M/C) cell reaction that results when the membrane impedance sufficiently exceeds the reaction impedance.

Figure 2:
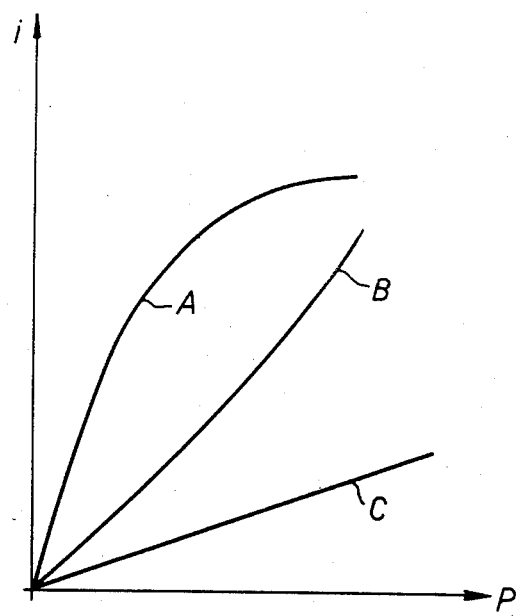
FIG. 2 is a diagrammatic presentation of a number of curves showing various forms of current versus hydrogen partial pressure dependencies.

FIG. 2 is a diagrammatic presentation of various current/pressure curves obtained with a commercial sensor (Orbisphere Laboratories, Model 2115/Pt) modified as explained in connection with FIG. 1; the central electrode was provided with a 0.3 mm surface layer of platinum by rolling which was polished to mirror brightness using a polishing paste with a grain size of below 0.5 μm.

The membranes used consisted of commercially available FEP (defined above in in Table I) in thicknesses of 0.5 mil (curve A), 1 mil (curve B) and 5 mil (curve C). Plotted on the ordinate is the current i, typically in microamperes, while the partial pressure P (=fugacity) of hydrogen in the ambient gas is plotted on the abscissa, typically in units of tenth of bars, or in units of $10^4$ Pascals. The electrolyte used was 1-normal aqueous sulfuric acid. The ambient fluids external to the membrane were gaseous mixtures of nitrogen and hydrogen with hydrogen fugacities between 0. and 1.4 bars.

Curve A indicates that the 0.5 mil FEP membrane is not suitable for the inventive method because after a relatively small increase of hydrogen fugacity, a "saturation" current or plateau was reached at about 130 μA. Once this plateau was reached, a further increase of the hydrogen fugacity did not cause a significant current change. This indicates R/C-operation due to preponderance of the reaction impedance.

Curve B, measured as curve A except that another membrane thickness was used, shows that a twofold increase of the thickness of the FEP membrane (to 1 mil) will improve the proportionality of the current-/fugacity relation but that this does not sufficiently increase the membrane impedance for the linearity of the current/fugacity relation that is indicative of M/C-operation.

Curve C of FIG. 2 shows that for the particular membrane material FEP a tenfold increase of membrane thickness over curve A (to 5 mil) is sufficient to achieve a strictly linear current/fugacity relation, i.e. a sufficient preponderance of membrane impedance over reaction impedance to achieve M/C-operation.

It will be apparent that each membrane material, in theory at least, will exhibit all three types of the current-/fugacity relation that correspond with curves A, B, C of FIG. 2. However, less suitable materials will show linearity (curve C) only at a membrane thickness that may be too high for practical purposes while preferred membrane materials with very low hydrogen permeation factors will already show linearity at a membrane thickness of 1 mil or even 0.5 mil.

In this context, it will be appreciated that the permeation factors cited above are given for purposes of comparison and quick orientation; the method used for their determination will be explained below but other methods that yield hydrogen permeation or permeability values suitable to avoid undue experimentation may be used as well. The essential common factor of any permeability determination suitable for use herein is linearity of response, i.e., the sensor used must be working within the range of linear response of the current to the hydrogen pressure.

The following examples are given to further illustrate the invention.

EXAMPLE 1

Hydrogen permeabilities of the membrane materials cited in Table I above were determined using a Model 2115 (Pt) sensor (Orbisphere Laboratories) as explained above in connection with FIGS. 1 and 2. The electrolyte was 1-normal aqueous sulfuric acid and a constant DC-voltage of 0.5 V was applied between the polished platinum anode and the Ag/AgCl cathodic counter electrode. Then, the hydrogen permeation value (HPV) of the membrane material in question was measured by providing the sensor with the test membrane material of known thickness, exposing the sensor to a test atmosphere of known hydrogen fugacity ($1 \cdot 10^5$ Pa), measuring the passage of current through the sensor, and calculating the HPV from the following relation:

$$HPV = \frac{\text{current}\left(\frac{\text{Coulomb}}{\text{second}}\right) \cdot \text{membrane thickness } (m)}{\text{electrode area } (m^2) \cdot 2 \text{ Faraday}\left(\frac{\text{Coulomb}}{\text{mol}}\right) \cdot H_2 \text{ pressure } (Pa)}$$

The factor 2 in the denominator is included because 2 Faraday of charge are added to one mole of molecular hydrogen in the electrode reaction.

A 1 mil ETFE membrane (thickness $25.4 \cdot 10^{-6}$ meters) produces a current of $37.5 \cdot 10^{-6}$ Coul/sec (37.5 μA) on the electrode area ($3.142 \cdot 10^{-5}$ m$^2$) at a hydrogen pressure of $10^5$ Pa, using $F = 9.64867 \cdot 10^4$ Coulomb per mole, i.e. an HPV of $1.57 \cdot 10^{-15}$ (mol·m/m$^2$·Pa·sec).

For convenience, the factor $10^{-15}$ is eliminated by giving the permeation factor in terms of nanomoles for hydrogen and micrometers for membrane thickness.

The following currents (μA) were measured with 1 mil films of the other materials and hydrogen pressures of $10^5$ Pa: PVF 2.5; PFA 140; FEP 100 and E-CTFE 3.61 and the hydrogen permeation factors calculated from these values are summarized in Table I above.

EXAMPLE 2

The sensor of example 1 with polished platinum disc-shaped anode (diameter 6.32 mm) and chloridized silver cathode was filled with an electrolyte containing 1 mol KCl and 1 mol HCl per liter of distilled water and fitted with a membrane made from 0.5 mil (12.7 μm) PVF. A potential of 0.7 V was applied between the anode and cathode of the detector, and the current in an atmosphere of 1 bar H$_2$ partial pressure was found to be 5 μA.

The relationship between measured current and hydrogen fugacity was found to be linear throughout the range from $10^{-3}$ bars up to 5 bars (equivalent to a range of dissolved hydrogen concentrations in water at 25° C. from 1.5 ppb to 7.5 ppm).

The response time at 25° C. was measured to be 5.2 seconds for 90% of total signal change.

Downward drift rates less than 1% per day were recorded over one week periods when the detector was exposed to a constant atmosphere of water saturated hydrogen at 1 bar total pressure.

Flow rates somewhat in excess of 200 ml/min were found to be suitable for valid measurements.

EXAMPLE 3

This example is given to illustrate that the needs of a particular application of the hydrogen detector influence the range of hydrogen partial pressures to be measured, and the response times which are acceptable. Some simple experiments will establish whether the membrane chosen meets these demands. Certain membranes may be less suitable on the grounds that they are too slow to respond, or so impermeable that the threshold of detectability is above the lower limit of the range of pressure to be measured. This is illustrated below using atypically thick membranes.

The sensor of example 2 was filled with 1-normal sulfuric acid as the electrolyte and fitted with 5 mil (127 μm) thick membranes of FEP, ETFE and E-CTFE. In each case its sensitivity was determined by measuring the current produced by the detector when exposed to a known partial pressure of hydrogen. The results are recorded in Table II.

Furthermore, the response of the detector to a step change of hydrogen partial pressure was determined, and analyzed according to diffusion theory (cf. example 4). The characteristic times $\tau = X_m^2/D_m$ determined from these analyses are also listed in Table II, as well as the 90% response times $0.305\tau$.

When the detector was exposed to pure nitrogen at 1 bar pressure the current measured was 1.5 nA independent of the nature of the membrane. Hydrogen partial pressures which generate detector currents less than 1.5 nA, therefore, are below the threshold of detectability.

For the detector fitted with a 5 mil FEP membrane, for example, this threshold is at:

$$\frac{1.5 \text{ (nA)}}{20100 \text{ (nA/bar)}} = 75\mu \text{ bar}$$

These thresholds are also recorded in Table II.

TABLE II

| Membranes | Sensitivity | τ (sec) | 90% resp. time | Lower limit of detectable H₂ pressure |
|---|---|---|---|---|
| E-CTFE | 0.75 μa/bar | 913 | 278 s | 2 mbar |
| ETFE | 7.46 " | 160 | 49 s | 200 μbar |
| FEP | 20.1 " | 72 | 22 s | 75 μbar |

EXAMPLE 4

The sensor of the preceding example was fitted with (A) a 5 mil ETFE membrane, (B) a 0.5 mil ETFE membrane, (C) a 5 mil ECTFE membrane and (D) a 5 mil FEP membrane, and in each case the response of the sensor to a defined step change of hydrogen partial pressure (fugacity) from a first pressure to a second pressure was measured at 25° C. and the results were analysed as to time/response behaviour.

According to diffusion theory, the detector current i observed at various times t after a sudden step change of hydrogen fugacity would be described in M/C-operation by $$\frac{i - i_0}{i_\infty - i_0} = 1 + 2 \sum_{n=1}^{\infty} (-1)^n \exp\left[-n^2 \pi^2 \frac{t}{\tau}\right]$$

where $i_0$ is the initial current, $i_\infty$ is the final steady state current and $\tau = X_m^2/D_m$ is a characteristic time for the crossing of the membrane by a molecule of dissolved gas (cf. Hale et al, J. Electroanal. Chem. 107 [1980]281). Accordingly, this provides for a simple method of analysis of experimental current-time data permitting to distinguish between M/C- and R/C-operation and a quick test is to compare the times for the detector to reach various fractions of the total signal change:

$$\frac{i - i_0}{i_\infty - i_0} \cdot 100 = n \text{ \% of total signal change}$$

Some of these times are as follows:

| | |
|---|---|
| 25% | 0.094 τ |
| 50% | 0.138 τ |
| 63.2% | 0.170 τ |
| 75% | 0.210 τ |
| 90% | 0.305 τ |
| 95% | 0.375 τ |
| 99% | 0.530 τ |

Hence, the ratio of the time for 75% change to that for 25% change should be $$0.210\tau/0.094\tau = 2.23$$

If similar ratios are found to fit the whole of the transient response then the current must be diffusion controlled, and linearity of the t versus t/τ function when operating a MEAC for hydrogen determination indicates M/C-operation of the sensor as required for the inventive method.

The following Table III represents the normalized current $$\frac{i - i_0}{i_\infty - i_0} \text{ "}(A - 1)\text{"},$$

time in seconds (or "A-2"), and the corresponding reduced time or t/τ value ("A-3") for the 5 mil ETFE membrane when measured in response to a hydrogen fugacity step from 0.1 bar to 0.3 bar (at 25° C.).

TABLE III

| A-1 (normalized current) | A-2 (seconds) | A-3 (t/τ) |
|---|---|---|
| 0.000 | 0 | — |
| 0.125 | 10 | 0.075 |
| 0.485 | 20 | 0.136 |
| 0.728 | 30 | 0.202 |
| 0.852 | 40 | 0.264 |
| 0.920 | 50 | 0.324 |
| 0.955 | 60 | 0.388 |

As A-3 indicates an essentially linear behaviour, the 5 mil ETFE membrane of the MEAC provides for M/C-operation in hydrogen determination according to the invention.

When repeating this measurement and with subsequent analysis under the same conditions as in (A) except using the 0.5 mil ETFE membrane (B) the results reported in Table IV were obtained.

TABLE IV

| B-1 (normalized current) | B-2 (seconds) | B-3 (t/τ) |
|---|---|---|
| 0.000 | 0 | — |
| 0.175 | 0.4 | 0.080 |
| 0.710 | 0.8 | 0.194 |
| 0.875 | 1.2 | 0.282 |
| 0.920 | 1.6 | 0.328 |
| 0.936 | 2.0 | 0.350 |
| 0.948 | 2.4 | 0.370 |
| 0.955 | 2.8 | 0.384 |

B-3 indicates non-linearity showing that the same membrane material ETFE that is suitable according to Table III for the inventive method when used in a thickness of 5 mil, does not provide a sufficiently high membrane impedance required for M/C-operation according to the invention when used in a thickness of only 0.5 mil.

Linearity of the $t/\tau$ versus t function was also established in this manner for membrane C with a hydrogen fugacity step from 1 to 2.19 bar at 25° C. and for membrane D with a hydrogen fugacity step from 0.1 to 0.3 bar, again at 25° C.

EXAMPLE 5

For the purpose of mathematical analysis of the inventive teaching, a formula for a sensor is established in which the impedance of the membrane and of the electrode reaction are of roughly the same magnitude.

Two equations are used to express the fact that the magnitude of the electric current must be equivalent, in the steady state and when written in appropriate units, to the net rate of entry of hydrogen into the sensor through the membrane, on the one hand, and to the rate of disappearance due to the electrochemical reaction of hydrogen from the electrolyte space adjacent to the electrode, on the other hand.

Hence:

$$i = \frac{2FA\, S_m D_m (P_o - P_i)}{X_m} \quad (1)$$

and $$i = 2FA\, k\, (P_i)^n \quad (2)$$

in which i symbolizes the electric current
F is the Faraday
A is the electrode area
$S_m$ is the solubility of hydrogen in the membrane
$D_m$ is the diffusion coefficient of hydrogen in the membrane
$P_o$ is the partial pressure of hydrogen acting on the outside of the membrane
$P_i$ is the partial pressure of hydrogen in the electrolyte between the membrane and the anode
k is a kinetic rate constant for the electro-oxidation of hydrogen at the anode n is the order of the oxidation reaction with respect to dissolved hydrogen and
$X_m$ is the membrane thickness.

Since an absolute maximum for the partial pressure of hydrogen inside the sensor is the partial pressure outside, that is:

$$P_i(\max) = P_o$$

an upper limit for the current must be $$i_l = 2FAkP_o^n$$

$P_i$ may then be eliminated from the equation since:

$$P_i = P_o(i/i_l)^{1/n}$$

The first equation above then becomes:

$$i = \frac{2FA\, S_m D_m P_o}{X_m}\left[1 - \left(\frac{i}{i_l}\right)^{1/n}\right]$$

This is the desired equation describing a MEAC in which either the membrane or the electrode reaction or both of these impedances control the magnitude of the detector current.

For comparison, the equation for the current magnitude at a MEAC used as an oxygen detector is recovered. As the electroreduction of oxygen is very rapid, that is k and $i_l \to \infty$, the term in $i/i_l$ can be neglected:

$$i = \frac{2FA\, S_m D_m P_o}{X_m} = i_d \quad (3)$$

This is the equation for the current at a MEAC limited by diffusion of reactant through the membrane. It has been symbolized by $i_d$ to emphasize the fact that diffusion is the rate controlling influence.

Further examination of the original equation shows that the diffusion controlled limit is reached when $$i_l \gg i_d \quad (4)$$

or $$P_o^{1-n} \frac{S_m D_m}{X_m} \ll k \quad (5)$$

At the opposite extreme, if the electrode reaction rate is very slow so that $$i_l \ll i_d \quad (6)$$

that is $$k \ll \frac{S_m D_m}{X_m} P_o^{1-n} \quad (7)$$

then the current magnitude is determined by the kinetics of the electrode reaction and $$i \to i_l = 2FAkP_o^n \quad (8)$$

As n~0 (zero order with respect to dissolved species), the current is not a measure of hydrogen concentration at this extreme.

The full formula applies to the full range of relative magnitudes of $i_l$ and $i_d$.

The consequence of this result is that only when the kinetic current limit $i_l$ sufficiently exceeds the membrane diffusion limit $i_d$ will the detector produce an output proportional to hydrogen partial pressure.

According to the art, this result is reached by increasing the raction rate to the extent that the reaction impedance is sufficiently reduced. According to the invention, the membrane material and/or membrane thickness is selected such that the inequality $$P_o^{1-n} \frac{S_m D_m}{X_m} << k \qquad (5)$$

is satisfied even though polished platinum is used at the anode surface.

The advantages of the present invention, as well as certain changes and modifications of the disclosed embodiments thereof, will be readily apparent to those skilled in the art. It is the applicant's intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. In the method of quantitative electroanalytical determination of elemental hydrogen in a fluid medium by means of an amperometric cell comprising at least two electrodes in contact with an aqueous electrolyte to provide a reaction impedance of said cell, said electrolyte being separated from said fluid medium by a membrane that is permeable to said elemental hydrogen but substantially impermeable to said electrolyte to provide a membrane impedance of said cell, said at least two electrodes comprising a first or anodic hydrogen sensing electrode and a second or cathodic counter electrode; the improvement consisting essentially of said first or anodic hydrogen sensing electrode having a substantially smooth sensing surface consisting essentially of a platinum metal, and of selecting said membrane impedance to exceed said reaction impedance sufficiently so as to provide for a membrane-controlled operation of said amperometric cell.

2. The method of claim 1, wherein said membrane-controlled operation of said cell is evidenced by an essentially linear current/pressure dependence.

3. The method of claim 1, wherein said membrane-controlled operation of said cell is evidenced by a downward drift of less than 1% per day.

4. The method of claim 1, wherein said membrane has a membrane impedance corresponding to a hydrogen permeation factor of below 10 (nmol·$\mu$m·m$^{-2}$·Pa$^{-1}$·s$^{-1}$).

5. The method of claim 4, wherein said membrane has a membrane impedance corresponding to a hydrogen permeation factor of below 1 (nmol·$\mu$m·m$^{-2}$·Pa$^{-1}$·s$^{-1}$).

6. The method of claim 5, wherein said membrane essentially consists of a hologen-containing polyene having a thickness of 10 to 50 $\mu$m.

7. The method of claim 4, wherein said membrane essentially consists of a hologen-containing polyene film having a thickness of below 300 $\mu$m.

8. The method of claim 7, wherein the halogen-containing polyene is selected from the group consisting of FEP, PFA, PVF, PTFE, ETFE and E-CTFE and wherein the film thickness is in the range of from 10 to 125 $\mu$m.

9. The method of claim 1, wherein said substantially smooth sensing surface has a ratio of apparent surface area:actual surface area in the range of from 1:1 to 1:3.

10. A method according to claim 1 wherein the two electrodes are polarized by constant DC voltage and wherein the aqueous electrolyte is acidic.

11. In a sensor for quantitative electroanalystical determination of elemental hydrogen in a fluid medium, said sensor including an amperometric cell comprising at least two electrodes in contact with an aqueous electrolyte to provide a reaction impedance of said cell, a membrane for separating said electrolyte from said fluid medium, said membrane being permeable to said elemental hydrogen but substantially impermeable to said electrolyte and providing a membrane impedance of said cell, said at least two electrodes comprising an anodic hydrogen sensing electrode and a cathodic counter electrode; the improvement consisting essentially of said anodic electrode having a substantially smooth sensing surface consisting of a platinum metal, and said membrane having a thickness in the range of from 10 to 300 $\mu$m and a hydrogen permeation factor of below 1 (nmol·$\mu$m·m$^{-2}$Pa$^{-1}$·s$^{-1}$), wherein said substantially smooth sensing surface of the platinum metal has a ratio of apparent surface area:actual surface area in the range of from 1:1 to 1:3.

12. In a sensor for quantitative electroanalytical determination of elemental hydrogen in a fluid medium, said sensor including an amperometric cell comprising at least two electrodes in contact with an aqueous electrolyte to provide a reaction impedance of said cell, a membrane for separating said electrolyte from said fluid medium, said membrane being permeable to said elemental hydrogen but substantially impermeable to said electrolyte and providing a membrane impedance of said cell, said at least two electrodes comprising an anodic hydrogen sensing electrode and a cathodic counter electrode; the improvement consisting essentially of said anodic electrode having a substantially smooth sensing surface consisting of a platinum metal, and said membrane having a thickness in the range of from 10 to 300 $\mu$m and a hydrogen permeation factor of below 1 (nmol·$\mu$m·m$^{-2}$·Pa$^{-1}$·s$^{-1}$) and the aqueous electrolyte is acidic.

13. A sensor according to claim 12 in which the reaction products produced at the cathode are unoxidizable at the anode.

* * * * *